US011045315B2

(12) United States Patent
Valencia et al.

(10) Patent No.: US 11,045,315 B2
(45) Date of Patent: Jun. 29, 2021

(54) METHODS OF STEERING AND DELIVERY OF INTRAVASCULAR DEVICES

(71) Applicant: Cephea Valve Technologies, Inc., Santa Clara, CA (US)

(72) Inventors: Francisco Valencia, East Palo Alto, CA (US); Sean A. McNiven, Menlo Park, CA (US); Randolf von Oepen, Aptos, CA (US)

(73) Assignee: CEPHEA VALVE TECHNOLOGIES, INC., Santa Clara, CA (US)

( * ) Notice: Subject to any disclaimer, the term of this patent is extended or adjusted under 35 U.S.C. 154(b) by 0 days.

(21) Appl. No.: 15/662,098

(22) Filed: Jul. 27, 2017

(65) Prior Publication Data

US 2018/0055636 A1    Mar. 1, 2018

Related U.S. Application Data

(60) Provisional application No. 62/436,913, filed on Dec. 20, 2016, provisional application No. 62/380,862, filed on Aug. 29, 2016.

(51) Int. Cl.
*A61F 2/24* (2006.01)
*A61M 25/01* (2006.01)

(52) U.S. Cl.
CPC .............. *A61F 2/2427* (2013.01); *A61F 2/24* (2013.01); *A61M 25/0138* (2013.01); *A61M 25/0147* (2013.01)

(58) Field of Classification Search
CPC ...... A61B 18/1492; A61B 2017/00243; A61B 2017/00323; A61B 2018/0037;
(Continued)

(56) References Cited

U.S. PATENT DOCUMENTS

| 4,406,656 A | 9/1983 | Hattler et al. |
| 4,728,319 A | 3/1988 | Masch |

(Continued)

FOREIGN PATENT DOCUMENTS

| CN | 1469724 A | 1/2004 |
| CN | 1688352 A | 10/2005 |

(Continued)

OTHER PUBLICATIONS

Takizawa H et al: "Development of a microfine active bending catheter equipped with MIF tactile sensors",Micro Electro Mechanical Systems, 1999. MEMS '99. Twelfth IEEE INTERNA TI0NAL Conference on Orlando, FL, USA Jan. 17-21, 1999, Piscataway, NJ, USA,IEEE, US, Jan. 17, 1999 (Jan. 17, 1999), pp. 412-417, XP010321677, ISBN: 978-0-7803-5194-3 figures 1-3.

(Continued)

*Primary Examiner* — Mohamed G Gabr
(74) *Attorney, Agent, or Firm* — Workman Nydegger

(57) ABSTRACT

A method of delivering a rigid intravascular device to a target location in a patient's heart includes positioning a distal tip of an elongated member of the intravascular device delivery system in a right atrium of a heart and moving the distal tip of the elongated member into a left atrium of the heart. The method includes advancing an inner steerable catheter of the elongated member longitudinally distally relative to an outer sleeve of the elongated member a first longitudinal distance; deflecting at least a portion of the inner steerable catheter a first deflection amount; then advancing an inner steerable catheter of the elongated member longitudinally distally relative to an outer sleeve of the elongated member a second longitudinal distance; and then deflecting at least a portion of the inner steerable catheter a second deflection amount.

22 Claims, 8 Drawing Sheets

(58) Field of Classification Search
CPC .. A61B 2018/00214; A61B 2018/1861; A61B 2018/00351; A61B 2018/00839; A61B 2018/00392; A61B 2018/00577; A61M 25/0138; A61M 25/0105; A61M 25/0133; A61M 2025/0161; A61F 2/246; A61F 2/2466

See application file for complete search history.

(56) References Cited

U.S. PATENT DOCUMENTS

| | | | |
|---|---|---|---|
| 5,053,043 | A | 10/1991 | Gottesman et al. |
| 5,059,213 | A | 10/1991 | Chesterfield et al. |
| 5,078,722 | A | 1/1992 | Stevens |
| 5,078,723 | A | 1/1992 | Dance et al. |
| 5,236,450 | A | 8/1993 | Scott |
| 5,325,845 | A | 7/1994 | Adair |
| 5,345,945 | A | 9/1994 | Hodgson et al. |
| 5,387,219 | A | 2/1995 | Rappe |
| 5,415,664 | A | 5/1995 | Pinchuk |
| 5,472,423 | A | 12/1995 | Gronauer |
| 5,571,085 | A | 11/1996 | Accisano, III |
| 5,662,606 | A | 9/1997 | Cimino et al. |
| 5,669,919 | A | 9/1997 | Sanders et al. |
| 5,769,812 | A | 6/1998 | Stevens et al. |
| 5,807,405 | A | 9/1998 | Vanney et al. |
| 5,820,591 | A | 10/1998 | Thompson et al. |
| 5,843,103 | A | 12/1998 | Wulfman |
| 5,855,601 | A | 1/1999 | Bessler et al. |
| 5,873,882 | A | 2/1999 | Straub et al. |
| 5,902,334 | A | 5/1999 | Dwyer et al. |
| 5,906,642 | A | 5/1999 | Caudillo et al. |
| 5,957,973 | A | 9/1999 | Quiachon et al. |
| 6,090,118 | A | 7/2000 | McGuckin, Jr. |
| 6,180,059 | B1 | 1/2001 | Divino, Jr. et al. |
| 6,228,110 | B1 | 5/2001 | Munsinger |
| 6,458,137 | B1 | 10/2002 | Klint |
| 6,517,550 | B1 | 2/2003 | Konya et al. |
| 6,695,836 | B1 | 2/2004 | DeMello et al. |
| 6,926,725 | B2 | 8/2005 | Cooke et al. |
| 7,172,617 | B2 | 2/2007 | Colgan et al. |
| 7,344,553 | B2 | 3/2008 | Opolski et al. |
| 7,666,204 | B2 | 2/2010 | Thornton et al. |
| 7,736,388 | B2 | 6/2010 | Goldfarb et al. |
| 7,837,727 | B2 | 11/2010 | Goetz et al. |
| 7,988,724 | B2 | 8/2011 | Salahieh et al. |
| 7,993,303 | B2 | 8/2011 | Von Oepen et al. |
| 8,157,852 | B2 | 4/2012 | Bloom et al. |
| 8,523,881 | B2 | 9/2013 | Cabiri et al. |
| 8,647,323 | B2 | 2/2014 | Guo et al. |
| 8,911,455 | B2 | 12/2014 | Quadri et al. |
| 8,926,588 | B2 | 1/2015 | Berthiaume et al. |
| 8,926,692 | B2 | 1/2015 | Dwork |
| 9,339,378 | B2 | 5/2016 | Quadri et al. |
| 9,370,423 | B2 | 6/2016 | Ryan |
| 9,393,112 | B2 | 7/2016 | Tuval et al. |
| 9,399,112 | B2 | 7/2016 | Shevgoor et al. |
| 9,668,859 | B2 | 6/2017 | Kheradvar et al. |
| 9,687,373 | B2 | 6/2017 | Vad |
| 9,693,862 | B2 | 7/2017 | Campbell et al. |
| 9,801,745 | B2 | 10/2017 | Wubbeling et al. |
| 10,111,671 | B2 | 10/2018 | Bodewadt |
| 10,117,760 | B2 | 11/2018 | Mangiardi |
| 10,376,673 | B2 | 8/2019 | Van Hoven et al. |
| 10,398,553 | B2 | 9/2019 | Kizuka |
| 10,470,902 | B2 | 11/2019 | Sheldon et al. |
| 2001/0002445 | A1 | 5/2001 | Vesely |
| 2001/0047150 | A1 | 11/2001 | Chobotov |
| 2002/0013547 | A1 | 1/2002 | Paskar |
| 2004/0049207 | A1* | 3/2004 | Goldfarb ............ A61M 25/0136 606/139 |
| 2004/0064179 | A1 | 4/2004 | Linder et al. |
| 2004/0116848 | A1 | 6/2004 | Gardeski et al. |
| 2004/0127849 | A1 | 7/2004 | Kantor |
| 2004/0133232 | A1 | 7/2004 | Rosenbluth et al. |
| 2004/0147826 | A1 | 7/2004 | Peterson |
| 2005/0038383 | A1 | 2/2005 | Kelley et al. |
| 2005/0085903 | A1 | 4/2005 | Lau |
| 2005/0137695 | A1 | 6/2005 | Salahieh et al. |
| 2005/0143809 | A1 | 6/2005 | Salahieh et al. |
| 2005/0256452 | A1 | 11/2005 | DeMarchi et al. |
| 2005/0259452 | A1 | 11/2005 | Cho |
| 2005/0283231 | A1 | 11/2005 | Haug et al. |
| 2005/0277874 | A1 | 12/2005 | Selkee |
| 2005/0277876 | A1 | 12/2005 | Hayden |
| 2005/0288768 | A1 | 12/2005 | Sowinski et al. |
| 2006/0135961 | A1 | 6/2006 | Rosenman et al. |
| 2007/0060997 | A1 | 3/2007 | de Boer |
| 2007/0156225 | A1 | 7/2007 | George et al. |
| 2007/0173757 | A1 | 7/2007 | Levine et al. |
| 2007/0197858 | A1 | 8/2007 | Goldfarb et al. |
| 2007/0203561 | A1 | 8/2007 | Forster et al. |
| 2007/0260225 | A1 | 11/2007 | Sakakine et al. |
| 2007/0270779 | A1 | 11/2007 | Jacobs et al. |
| 2007/0299424 | A1 | 12/2007 | Cumming et al. |
| 2008/0103585 | A1 | 5/2008 | Monstadt et al. |
| 2008/0109065 | A1 | 5/2008 | Bowe |
| 2008/0188850 | A1 | 8/2008 | Mody et al. |
| 2008/0195126 | A1 | 8/2008 | Solem |
| 2009/0036768 | A1 | 2/2009 | Seehusen et al. |
| 2009/0069885 | A1 | 3/2009 | Rahdert et al. |
| 2009/0099554 | A1 | 4/2009 | Forster et al. |
| 2009/0163934 | A1 | 6/2009 | Raschdorf, Jr. et al. |
| 2009/0182407 | A1 | 7/2009 | Leanna et al. |
| 2009/0204005 | A1 | 8/2009 | Keast et al. |
| 2009/0240326 | A1 | 9/2009 | Wilson et al. |
| 2009/0276039 | A1 | 11/2009 | Meretei |
| 2009/0281619 | A1 | 11/2009 | Le et al. |
| 2010/0004739 | A1 | 1/2010 | Vesely |
| 2010/0044410 | A1 | 2/2010 | Argentine et al. |
| 2010/0059173 | A1 | 3/2010 | Kampa et al. |
| 2010/0070009 | A1 | 3/2010 | Barker |
| 2010/0217261 | A1* | 8/2010 | Watson ............. A61B 18/1492 606/41 |
| 2010/0249894 | A1 | 9/2010 | Oba et al. |
| 2010/0331776 | A1 | 12/2010 | Salahieh et al. |
| 2011/0112630 | A1 | 5/2011 | Groothuis et al. |
| 2011/0166566 | A1 | 7/2011 | Gabriel |
| 2011/0166649 | A1 | 7/2011 | Gross et al. |
| 2011/0202128 | A1 | 8/2011 | Duffy |
| 2011/0257718 | A1 | 10/2011 | Argentine |
| 2011/0307049 | A1 | 12/2011 | Kao |
| 2012/0022640 | A1 | 1/2012 | Gross et al. |
| 2012/0065464 | A1 | 3/2012 | Elllis et al. |
| 2012/0109078 | A1 | 5/2012 | Schaeffer |
| 2012/0172915 | A1 | 7/2012 | Fifer et al. |
| 2012/0316639 | A1 | 12/2012 | Kleinschrodt |
| 2012/0330348 | A1 | 12/2012 | Strauss et al. |
| 2012/0330408 | A1 | 12/2012 | Hillukka et al. |
| 2013/0030514 | A1 | 1/2013 | Kasprzak et al. |
| 2013/0041314 | A1 | 2/2013 | Dillon |
| 2013/0066342 | A1 | 3/2013 | Dell et al. |
| 2013/0103001 | A1 | 4/2013 | Benmaamer et al. |
| 2013/0109910 | A1 | 5/2013 | Alexander et al. |
| 2013/0131775 | A1 | 5/2013 | Hadley et al. |
| 2013/0289696 | A1 | 10/2013 | Maggard et al. |
| 2014/0107693 | A1 | 4/2014 | Plassman |
| 2014/0114390 | A1 | 4/2014 | Tobis et al. |
| 2014/0142688 | A1 | 5/2014 | Duffy et al. |
| 2014/0148889 | A1 | 5/2014 | Deshmukh et al. |
| 2014/0180124 | A1 | 6/2014 | Whiseant et al. |
| 2014/0200649 | A1 | 7/2014 | Essinger et al. |
| 2014/0228871 | A1 | 8/2014 | Cohen et al. |
| 2014/0276966 | A1 | 9/2014 | Ranucci et al. |
| 2014/0324164 | A1 | 10/2014 | Gross et al. |
| 2014/0336744 | A1 | 11/2014 | Tani et al. |
| 2014/0379074 | A1* | 12/2014 | Spence ............. A61F 2/2409 623/2.11 |
| 2015/0005704 | A1 | 1/2015 | Heisel et al. |
| 2015/0005801 | A1 | 1/2015 | Marquis et al. |
| 2015/0088189 | A1 | 3/2015 | Paul, Jr. |
| 2015/0112430 | A1 | 4/2015 | Creaven et al. |
| 2015/0272759 | A1 | 10/2015 | Argentine |
| 2015/0306806 | A1 | 10/2015 | Dando et al. |

(56) References Cited

U.S. PATENT DOCUMENTS

| | | |
|---|---|---|
| 2016/0045311 A1 | 2/2016 | McCann et al. |
| 2016/0074163 A1 | 3/2016 | Yang et al. |
| 2016/0113765 A1 | 4/2016 | Ganesan et al. |
| 2016/0143661 A1 | 5/2016 | Wood et al. |
| 2017/0035566 A1 | 2/2017 | Krone et al. |
| 2017/0042678 A1 | 2/2017 | Ganesan et al. |
| 2017/0080186 A1 | 3/2017 | Salahieh et al. |
| 2017/0232238 A1 | 8/2017 | Biller et al. |
| 2018/0028177 A1 | 2/2018 | Van et al. |
| 2018/0028215 A1 | 2/2018 | Cohen |
| 2018/0028305 A1 | 2/2018 | Von et al. |
| 2018/0028779 A1 | 2/2018 | Von et al. |
| 2018/0028787 A1 | 2/2018 | McNiven et al. |
| 2018/0055637 A1 | 3/2018 | Von et al. |
| 2018/0056033 A1 | 3/2018 | Von et al. |
| 2018/0056043 A1 | 3/2018 | Von et al. |
| 2018/0071098 A1 | 3/2018 | Alon |
| 2018/0092744 A1 | 4/2018 | von Oepen et al. |
| 2018/0126119 A1 | 5/2018 | McNiven et al. |
| 2018/0132837 A1* | 5/2018 | Mathena ............... A61M 29/00 |
| 2018/0133454 A1 | 5/2018 | Von et al. |
| 2018/0360457 A1 | 12/2018 | Ellis et al. |
| 2019/0030285 A1 | 1/2019 | Prabhu et al. |
| 2019/0274831 A1 | 9/2019 | Prabhu |
| 2020/0155804 A1 | 5/2020 | von Oepen et al. |
| 2020/0230352 A1 | 7/2020 | Mcniven et al. |
| 2020/0230354 A1 | 7/2020 | Von Oepen et al. |

FOREIGN PATENT DOCUMENTS

| | | |
|---|---|---|
| CN | 1961983 A | 5/2007 |
| CN | 101247847 A | 8/2008 |
| CN | 101426452 A | 5/2009 |
| CN | 101506538 A | 8/2009 |
| CN | 102159277 A | 8/2011 |
| CN | 102258402 A | 11/2011 |
| CN | 102481433 A | 5/2012 |
| CN | 102548505 A | 7/2012 |
| CN | 102770080 A | 11/2012 |
| CN | 102933161 A | 2/2013 |
| CN | 103517689 A | 1/2014 |
| CN | 103702635 A | 4/2014 |
| CN | 103841899 A | 6/2014 |
| CN | 103957993 A | 7/2014 |
| CN | 104203329 A | 12/2014 |
| CN | 104812439 A | 7/2015 |
| CN | 105246434 A | 1/2016 |
| CN | 105899167 A | 8/2016 |
| EP | 1980288 | 10/2008 |
| EP | 2537487 | 12/2012 |
| EP | 2702965 A1 | 3/2014 |
| EP | 3009103 A1 | 4/2016 |
| JP | 2003062072 | 3/2003 |
| JP | 2006-528911 A | 12/2006 |
| JP | 2013-516244 A | 5/2013 |
| WO | 01/51114 A2 | 7/2001 |
| WO | WO 2007044285 | 4/2007 |
| WO | WO 2007136829 | 11/2007 |
| WO | WO 2008103722 | 8/2008 |
| WO | 2010/024801 A1 | 3/2010 |
| WO | WO 2010121076 | 10/2010 |
| WO | WO 2012020521 | 2/2012 |
| WO | 2012/057983 A1 | 5/2012 |
| WO | 2012/151396 A2 | 11/2012 |
| WO | 2013/126529 A2 | 8/2013 |
| WO | 2014/064694 A2 | 5/2014 |
| WO | WO 2014121280 | 8/2014 |
| WO | WO 2014128705 | 8/2014 |
| WO | 2015/191938 A1 | 12/2015 |
| WO | WO 2016022797 | 2/2016 |
| WO | WO 2016112085 | 7/2016 |
| WO | WO 2016144708 | 9/2016 |
| WO | WO 2016150806 | 9/2016 |
| WO | 2016/183526 A1 | 11/2016 |
| WO | 2017/023534 A2 | 2/2017 |
| WO | 2018/023038 A1 | 2/2018 |
| WO | 2018/023043 A1 | 2/2018 |
| WO | 2018/023045 A1 | 2/2018 |
| WO | WO 2018023044 | 2/2018 |
| WO | WO 2018023052 | 2/2018 |
| WO | 2018/044447 A1 | 3/2018 |
| WO | 2018/044448 A1 | 3/2018 |
| WO | 2018/044449 A1 | 3/2018 |
| WO | WO 2018044446 | 3/2018 |
| WO | 2018/067788 A1 | 4/2018 |
| WO | 2018/093426 A1 | 5/2018 |

OTHER PUBLICATIONS

U.S. Appl. No. 15/724,499, Mar. 25, 2020, Office Action.
U.S. Appl. No. 15/662,001, Mar. 24, 2020, Notice of Allowance.
U.S. Appl. No. 15/662,013, Jun. 13, 2019, Office Action.
U.S. Appl. No. 15/662,013, Oct. 10, 2019, Office Action.
U.S. Appl. No. 15/662,066, Feb. 27, 2019, Advisory Action.
U.S. Appl. No. 15/662,076, Jan. 31, 2019, Notice of Allowance.
U.S. Appl. No. 15/662,008, Jan. 31, 2019, Notice of Allowance.
U.S. Appl. No. 15/662,066, May 21, 2020, Office Action.
U.S. Appl. No. 15/662,089, Jun. 11, 2020, Office Action.
U.S. Appl. No. 15/662,093, Jul. 9, 2020, Advisory Action.
U.S. Appl. No. 15/724,499, Jul. 1, 2020, Notice of Allowance.
U.S. Appl. No. 15/662,013, May 7, 2020, Notice of Allowance.
U.S. Appl. No. 15/662,093, May 6, 2020, Office Action.
U.S. Appl. No. 15/662,142, Apr. 17, 2020, Office Action.
Advisory Action received for U.S. Appl. No. 15/662,013, dated Dec. 5, 2019.
Advisory Action received for U.S. Appl. No. 15/662,142, dated Dec. 20, 2019.
Notice of Allowance received for U.S. Appl. No. 15/662,001, dated Dec. 18, 2019.
Notice of Allowance received for U.S. Appl. No. 15/662,076, dated Oct. 8, 2019.
Notice of Allowance received for U.S. Appl. No. 15/724,499, dated Jul. 15, 2019.
Notice of Allowance received for U.S. Appl. No. 15/724,499, dated Nov. 22, 2019.
Office Action received for U.S. Appl. No. 15/662,001, dated Jun. 20, 2019.
Office Action received for U.S. Appl. No. 15/662,001, dated Oct. 4, 2019.
Office Action received for U.S. Appl. No. 15/662,008, dated Sep. 13, 2019.
Office Action received for U.S. Appl. No. 15/662,066, dated Dec. 16, 2019.
Office Action received for U.S. Appl. No. 15/662,066, dated Jul. 11, 2019.
Office Action received for U.S. Appl. No. 15/662,089, dated Jan. 10, 2020.
Office Action received for U.S. Appl. No. 15/662,089, dated Oct. 7, 2019.
Office Action received for U.S. Appl. No. 15/662,093, dated Aug. 29, 2019.
Office Action received for U.S. Appl. No. 15/662,093, dated Dec. 3, 2019.
Office Action received for U.S. Appl. No. 15/662,093, dated Mar. 7, 2019.
Supplemental Notice of Allowance received for U.S. Appl. No. 15/724,499, dated Aug. 27, 2019.

* cited by examiner

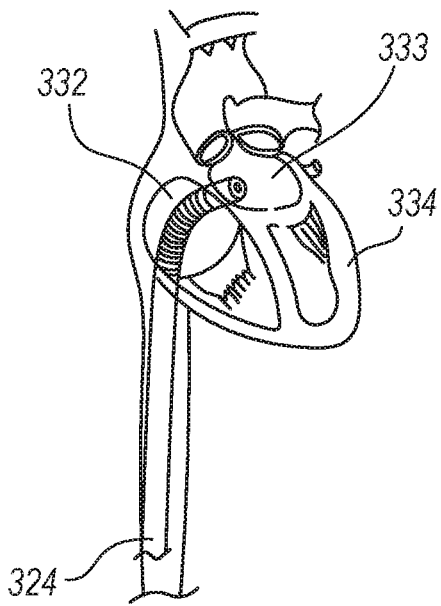
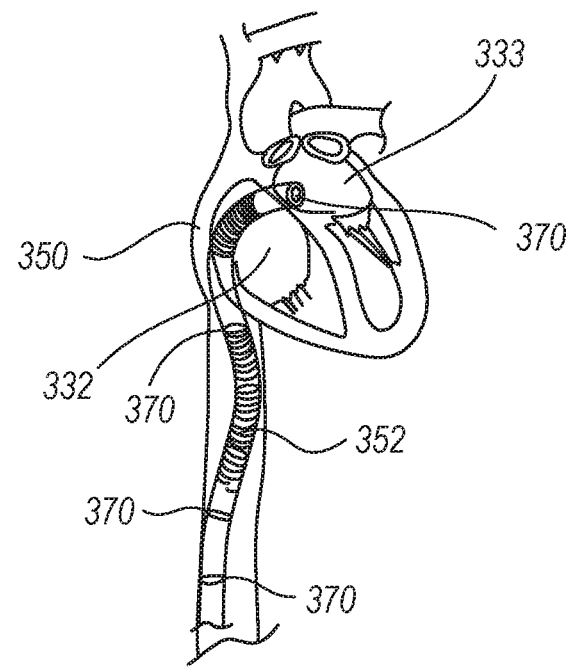
FIG. 8A
FIG. 8B
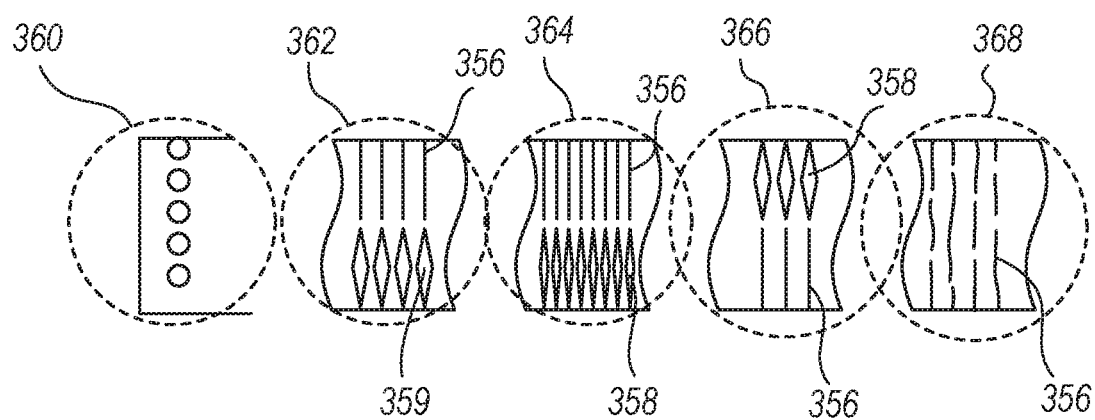
FIG. 9 ly small access incisions. An intravascular procedure may, for example, eliminate the need for open-heart surgery, reducing risks, costs, and time associated with an open-heart procedure. The intravascular procedure also enables faster recovery times with lower associated costs and risks of complication. An example of an intravascular procedure that significantly reduces procedure and recovery time and cost over conventional open surgery is a heart valve replacement or repair procedure. An artificial valve is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more wires positioned inside the catheter. Precise control of the distal end of the catheter allows for more reliable and faster positioning of a medical device and/or implant and other improvements in the procedures.

METHODS OF STEERING AND DELIVERY OF INTRAVASCULAR DEVICES

CROSS-REFERENCE TO RELATED APPLICATIONS

This application claims the benefit of and priority to U.S. Provisional Patent Application Ser. No. 62/380,862 filed on Aug. 29, 2016 and entitled "Methods of Steering and Delivery of Intravascular Devices," and to U.S. Provisional Patent Application Ser. No. 62/436,913 filed on Dec. 20, 2016 and entitled "Methods of Steering and Delivery of Intravascular Devices," which applications are expressly incorporated herein by reference in their entirety.

BACKGROUND OF THE DISCLOSURE

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication. An example of an intravascular procedure that significantly reduces procedure and recovery time and cost over conventional open surgery is a heart valve replacement or repair procedure. An artificial valve is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more wires positioned inside the catheter. Precise control of the distal end of the catheter allows for more reliable and faster positioning of a medical device and/or implant and other improvements in the procedures.

The devices can also be directed through the valve chordae or papillary muscles, for example, for interventional therapy to the mitral valve. When such procedures require the use of more than one instrument, each instrument would be dependent upon proper positioning in relation to the valve. Therefore, positioning or steering mechanisms need to be built into each instrument. This adds further cost, complexity, and time to the procedures.

Other procedures may include tracking a catheter and/or access sheath from a puncture in the femoral vein through the intra-atrial septum to the left atrium. This pathway may be used to access the left atrium for ablation of the atrium wall or ablation around the pulmonary veins. Such interventional therapies would require precise alignment with target areas for proper ablation placement. Additionally, alternative access routes and/or access routes to other cavities may be desired.

The scope of intravascular procedures has increased in recent years with more intravascular devices delivered to the heart through the patient's vasculature. Intravascular device delivery utilizes comparatively small radius turns through torturous anatomy that limits the capacity of the intravascular device delivery system to deliver intravascular devices of different dimensions.

BRIEF SUMMARY OF THE DISCLOSURE

In an embodiment, a method of delivering an intravascular device includes positioning a distal tip of an elongated member of the intravascular device delivery system in a right atrium of a heart; moving the distal tip of the elongated member into a left atrium of the heart; advancing an inner steerable catheter of the elongated member longitudinally distally relative to an outer sleeve of the elongated member a first longitudinal distance; deflecting at least a portion of the inner steerable catheter a first deflection amount; advancing an inner steerable catheter of the elongated member longitudinally distally relative to an outer sleeve of the elongated member a second longitudinal distance; and deflecting at least a portion of the inner steerable catheter a second deflection amount.

This summary is provided to introduce a selection of concepts that are further described below in the detailed description. This summary is not intended to identify specific features of the claimed subject matter, nor is it intended to be used as an aid in limiting the scope of the claimed subject matter.

Additional features of embodiments of the disclosure will be set forth in the description that follows. The features of such embodiments may be realized by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof that are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which:

FIG. 2-1 is a flowchart illustrating an embodiment of a method of positioning a rigid intravascular device in a heart;

FIG. 2-2 is a flowchart illustrating an embodiment of a method of delivering a rigid intravascular device in an operating setting to a target location in a heart;

FIG. 6-1 is a cross-sectional view of the embodiment of an intravascular device delivery system of FIG. 3 with the inner steerable catheter translated axial from the outer steerable catheter;

FIG. 6-2 is a cross-sectional view of the embodiment of an intravascular device delivery system of FIG. 3 with a bend in the inner steerable catheter.

FIG. 8A graphically depicts a path generally taken by a conventional delivery catheter through the right atrium of the heart and through the intra-atrial septum.

FIG. 8B graphically depicts an improved path for the delivery catheter by use of various cut patterns in different sections of the delivery catheter.

FIG. 9 is a graphical representation of various cut patterns that can be used in different sections of the delivery catheter to achieve a desired shape or bending of the delivery catheter.

DETAILED DESCRIPTION

Figure 1:
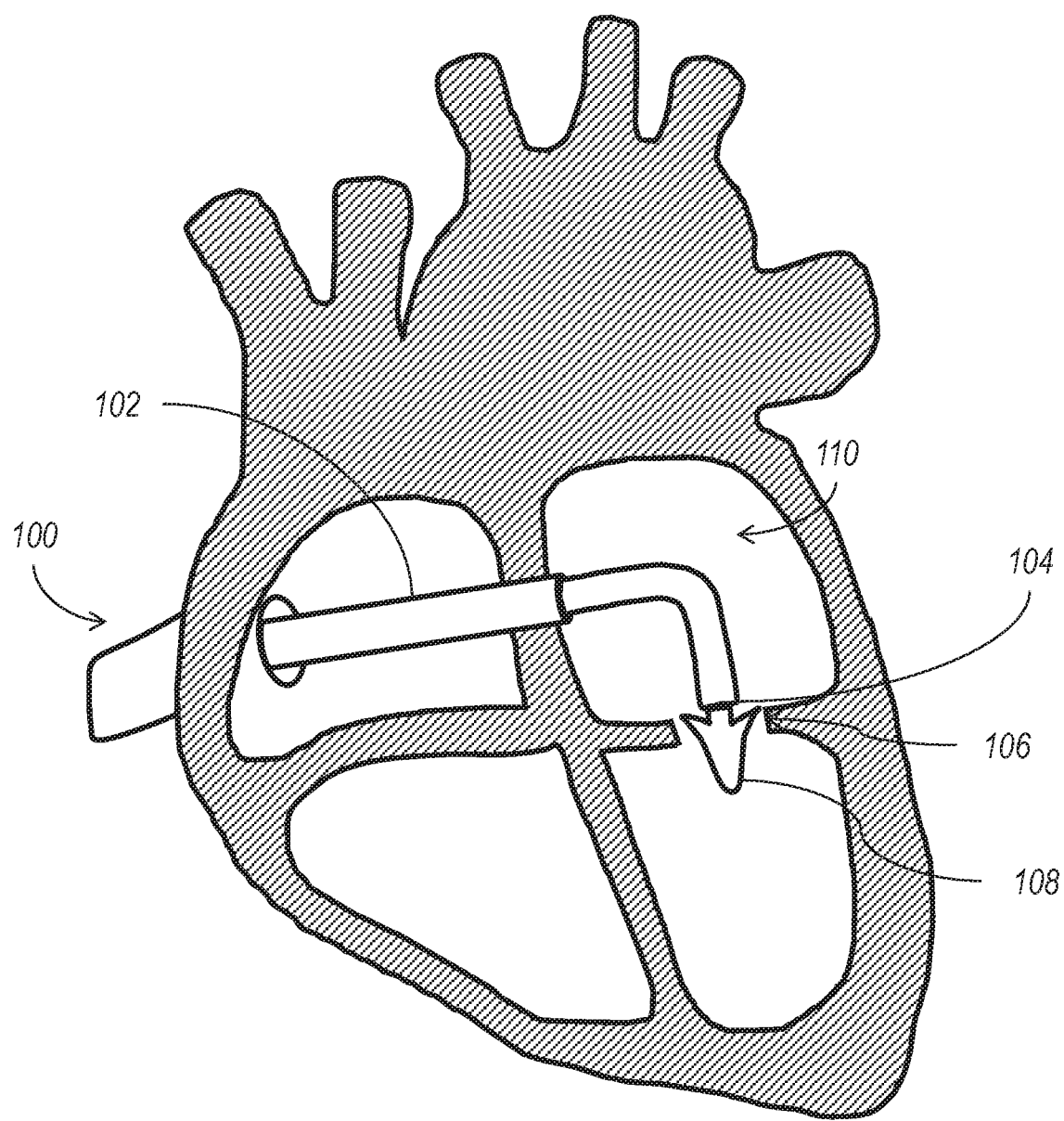
FIG. 1 is a schematic representation of an intravascular device delivery system delivering a flexible intravascular device in a heart.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to manufacturing and using intravascular device delivery systems or other steerable intravascular systems. An intravascular device delivery system may allow a medical professional to deliver an intravascular or other medical device to a target location in a patient's body. While the present disclosure will describe intravascular device delivery systems and applications thereof in relation to intravascular procedures in the heart, it should be understood that the devices, systems, and methods described herein may be applicable to other bodily lumens and/or cavities. Additionally, elements described in relation to any embodiment depicted and/or described herein may be combinable with elements described in relation to any other embodiment depicted and/or described herein. For example, any element described in relation to an embodiment depicted in FIG. 1 may be combinable with any element of an embodiment described in FIG. 3, and any element described in relation to an embodiment described in FIG. 6-2 may be combinable with any element of an embodiment depicted in FIG. 3.

An intravascular device delivery system includes a flexible elongated member that has a distal end and a proximal end. A handle is connected to a proximal end of the elongated member to allow a user, such as a medical professional and/or clinician, to control one or more movements of the elongated member. An intravascular device is positioned at and/or connected to the distal end of the elongated member.

In some embodiments, the elongated member includes a plurality of elements. For example, the elongated member may include a plurality of elements that extend from the proximal end to the distal end. In some embodiments, at least one of the elements of the elongated member includes a plurality of lumens therethrough to allow steerability of the element. In at least one embodiment, at least one element of the elongated member is steerable in at least two planes.

In some embodiments, the handle may include one or more controls (e.g., a knob, a button, a lever, or other controls) that may move at least one part of the intravascular device delivery system relative to another. For example, the handle may include one or more controls for moving at least one element of the elongated member relative to another element of the elongated member. The handle may move an inner element relative to an outer element of the elongated member in a proximal direction, in a distal direction, in a rotational direction, or combinations thereof.

FIG. 1 illustrates an intravascular device delivery system 100 that includes an elongated member 102 with a distal tip 104 positioned proximate a target location, such as the mitral annulus 106 of the heart. The intravascular device delivery system 100 includes the elongated member 102 and an intravascular device 108 that is deliverable through the elongated member 102 to the target location.

The elongated member 102 of the intravascular device delivery system 100 is steerable to the distal tip 104, allowing the distal tip 104 to be located at the target location after entering the left atrium 110 of the heart. A intravascular device 108 is then urged longitudinally through the elongated member 102 to the distal tip 104 and is deployed at the target location. The confines of the left atrium 110, however, may limit the mobility of a rigid intravascular device once the rigid intravascular device is within the left atrium 110.

Figures 1, 2:
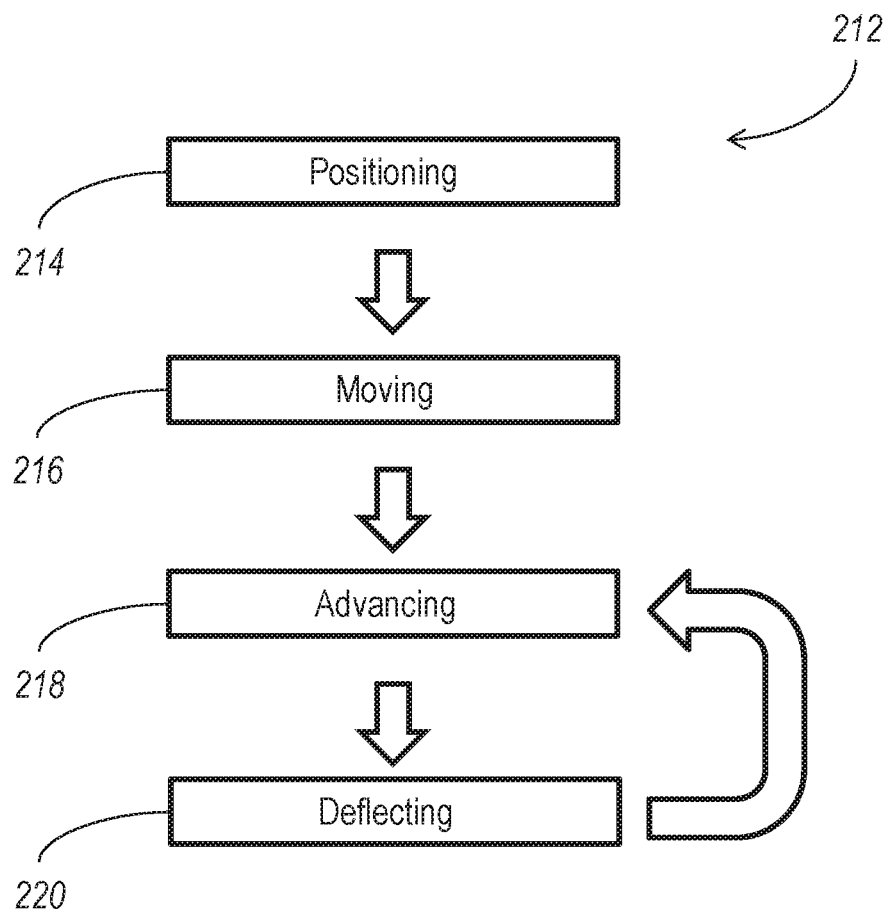
Figure 2:
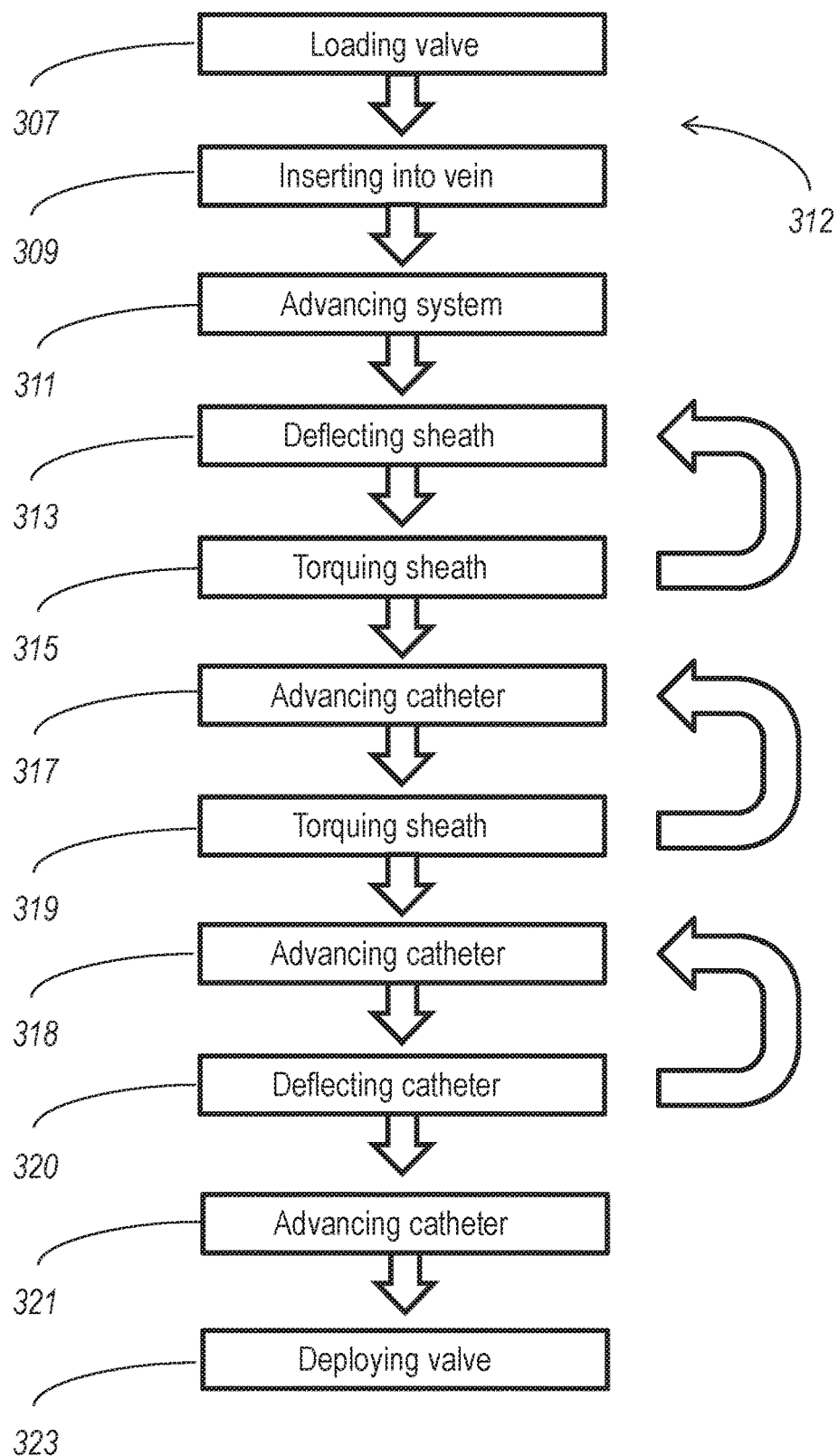

FIG. 2-1 is a flowchart 212 illustrating an embodiment of a method of positioning a rigid intravascular device at a target location in a patient's heart. In some embodiments, the method includes positioning 214 a rigid intravascular device distal the distal tip of an elongated member of an intravascular device delivery system. The method further includes moving 216 the rigid intravascular device and elongated member together through the intra-atrial septum and into the left atrium.

The method further includes advancing 218 the rigid intravascular device and an inner steerable catheter relative to an outer sleeve of the elongated member while deflecting 220 the inner steerable catheter toward the mitral annulus. In some embodiments, advancing 218 the rigid intravascular device and deflecting 220 the inner steerable catheter occur simultaneously. In other embodiments, advancing 218 the rigid intravascular device and inner steerable catheter and deflecting 220 the inner steerable catheter occur in an alternating, iterative fashion (e.g., advancing 218 the replacement valve and inner steerable catheter a first time, deflecting 220 the inner steerable catheter a first time, advancing 218 the replacement valve and inner steerable catheter a second time, and deflecting 220 the inner steerable catheter a second time). An operator may advance the rigid intravascular device and inner steerable catheter and deflect the inner steerable catheter as many times as necessary to position the rigid intravascular device at the target location before deploying the rigid intravascular device.

In at least one embodiment, the method further includes advancing the outer sleeve relative to the intra-atrial septum after deflecting 220 the inner steerable catheter to orient the rigid intravascular device toward and/or in the mitral annulus.

FIG. 2-2 is a flowchart illustrating an embodiment of a more complete operative method of delivering a replacement valve intravascular device, according to the present disclosure. For example, the embodiment illustrated includes loading 307 the valve onto a distal tip of an elongated member (such as distal tip 104 of elongated member 102 described herein) and inserting 309 the intravascular device delivery system and replacement valve into the patient's vein.

Loading a replacement valve onto and/or into a distal tip of an elongated member may include rinsing the valve or other intravascular device in sterile water or saline. After removing storage or transportation fluids or other coatings from the replacement valve, the device is collapsed in a radial direction to a collapsed state during loading. The replacement valve may be immersed the valve in a cold water or saline bath. For example, a replacement valve with one or more shape-memory material components may be biased to expand radially at room and/or body temperature. The cold water or saline bath lowers the temperature of the replacement valve below a transformation temperature of the device, easing the transition to the collapsed state of the device.

The replacement valve may be loaded in to a loading device, such as a cone or other tapered structure. At least a portion of the elongated member of the intravascular device delivery system (e.g., a guidewire and/or guidewire lumen with an atraumatic tip) is inserted through the valve and distally beyond the valve such that the portion of the elongated member of the intravascular device delivery system extends completely through the replacement valve. The loading device is then advanced over the replacement valve to radially compress the replacement valve without folding or creasing the replacement valve. In at least one embodiments, an outer sleeve of the elongated member is moved in a distal direction (i.e., toward the replacement valve) to capture the collapsed replacement valve and retain the replacement valve in the distal tip of the elongated member.

As described herein, the intravascular device may be loaded into the patient's femoral artery to provide vascular access to the heart by advancing 311 the intravascular device delivery system through the femoral vein and into the heart via the inferior vena cava.

Once positioned in the right atrium of the heart, the intravascular device delivery system is oriented in the heart and toward the intra-atrial septum by deflecting 313 a steerable guide sheath of the elongated member and torquing 315 the steerable guide sheath. The intravascular device delivery system is oriented by iteratively and/or simultaneously deflecting 313 and torquing 315 the steerable guide sheath until the distal tip and/or guidewire of the intravascular system is properly oriented with respect to the intra-atrial septum.

The intravascular device (i.e., the replacement valve) is positioned into the left atrium of the heart by advancing 317 the inner steerable catheter relative to the steerable guide sheath and torquing 319 the steerable guide sheath. Similar to deflecting 313 and torquing 315 the steerable guide sheath described above, advancing 317 the inner steerable catheter relative to the steerable guide sheath and torquing 319 the steerable guide sheath may be performed iteratively and/or simultaneously until the replacement valve is positioned in the right atrium and the bending plane of the inner steerable catheter is aligned with the target location in the heart (e.g., the mitral annulus).

The method further includes advancing 318 the rigid intravascular device and an inner steerable catheter relative to a steerable guide sheath of the elongated member while deflecting 320 the inner steerable catheter toward the mitral annulus. In some embodiments, advancing 318 the replacement valve and deflecting 320 the inner steerable catheter occur simultaneously. In other embodiments, advancing 318 the replacement valve and inner steerable catheter and deflecting 320 the inner steerable catheter occur in an alternating, iterative fashion (e.g., advancing 318 the replacement valve and inner steerable catheter a first time, deflecting 320 the inner steerable catheter a first time, advancing 318 the replacement valve and inner steerable catheter a second time, and deflecting 320 the inner steerable catheter a second time). An operator may advance the rigid intravascular device and inner steerable catheter and deflect the inner steerable catheter as many times as necessary to position the replacement valve above the target location before advancing 321 the catheter to center the replacement valve in the target location and at least partially deploying 323 the replacement valve from the intravascular device delivery system.

Figure 3:
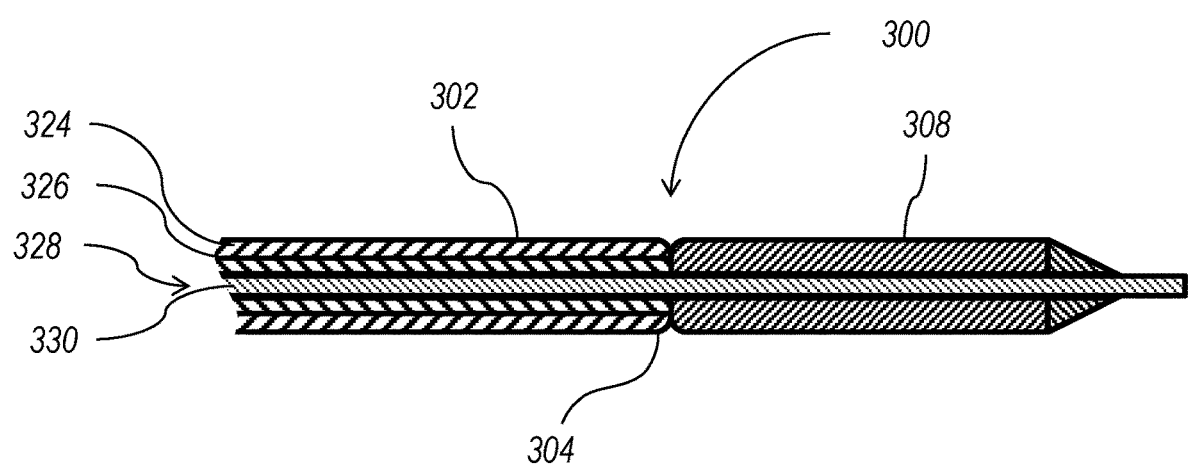
FIG. 3 is a schematic partial cutaway diagram of an embodiment of a rigid intravascular device positioned at a distal end of an elongated member of an intravascular device delivery system.

At least one illustrative embodiment of the method shown in FIG. 2-1 and part of the method shown in FIG. 2-2 is depicted in FIG. 3 through FIG. 7. FIG. 3 is a side view of an intravascular device delivery system 300, according to the present disclosure. The rigid intravascular device 308 is shown positioned at (e.g., in contact with) the distal tip 304 of the elongated member 302 of the intravascular device delivery system 300. In some embodiments, the rigid intravascular device 308 has a longitudinal length of 10 millimeters (mm), 20 mm, 30 mm, 40 mm, 50 mm, or any length therebetween that is substantially rigid. For example, the rigid intravascular device 308 may have at least 10 mm of the rigid intravascular device 308 that is rigid and may not pass through a curved catheter. Therefore, the rigid intravascular device 308 is positioned at the distal tip 304 of the elongated member 302 and is advanced through the patient's vasculature at the distal tip 304 of the elongated member 302 and/or at least partially external to the elongated member 302.

FIG. 3 also illustrates a plurality of elements in the elongated member 302. In some embodiments, the elongated member 302 includes at least an outer sleeve 324 and an inner steerable catheter 326 positioned radially within the outer sleeve 324. The inner steerable catheter 326 may have a lumen 328 therethrough that may allow a guidewire 330 to be moved longitudinally through the elongated member 302. In some embodiments, the rigid intravascular device 308 is positioned at the distal end of the inner steerable catheter 326. In other embodiments, the rigid intravascular device 308 is connected to the distal end of the inner steerable catheter 326.

In some embodiments, the outer sleeve 324 is a steerable catheter, such as a steerable guide catheter, that is steerable in at least one plane. In other embodiments, the outer sleeve 324 is steerable in at least two planes. In yet other embodiments, the outer sleeve 324 is not steerable and steering of the elongated member 302 relies upon the inner steerable catheter 326 and/or other elements of the elongated member 302.

Figure 4:
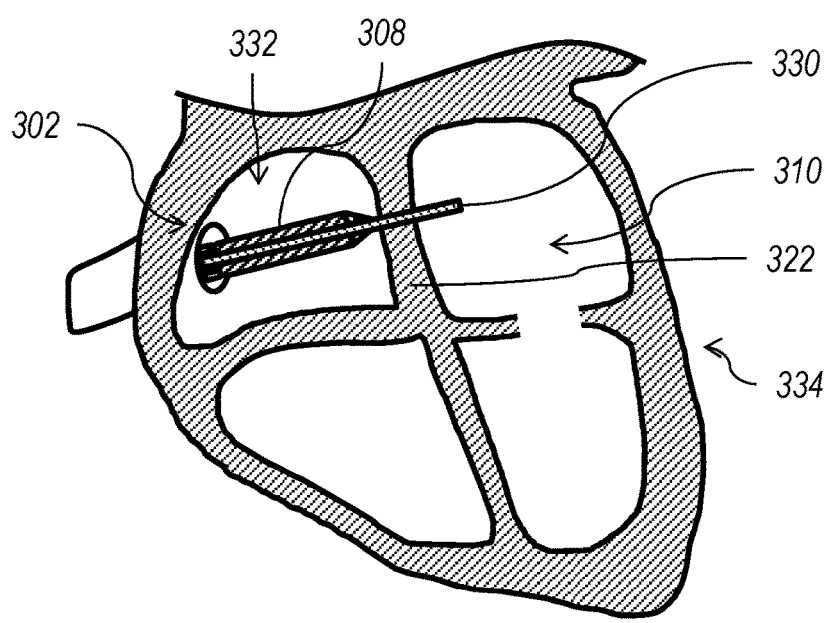
FIG. 4 is a cross-sectional view of the embodiment of an intravascular device delivery system of FIG. 3 in a right atrium.

FIG. 4 illustrates the embodiment of an elongated member 302 and rigid intravascular device 308 of FIG. 3 positioned in a right atrium 332 of a heart 334. A guidewire 330 may be inserted through the intra-atrial septum and into the left atrium 310 of the heart 334. The rigid intravascular device 308 is then urged longitudinally through the intra-atrial septum 322 to the left atrium 310, as shown in FIG. 5.

Figure 5:
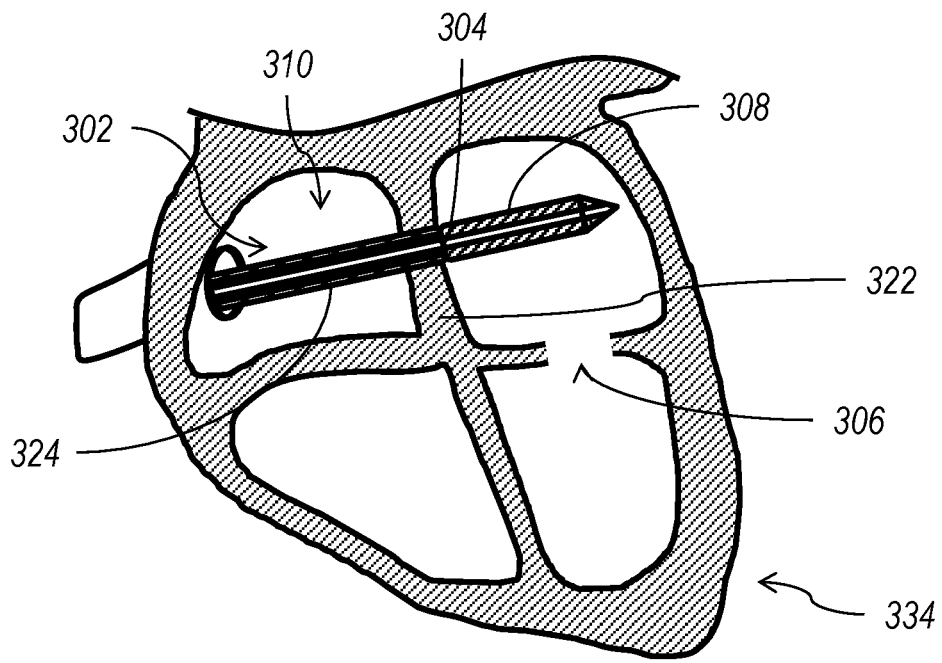
FIG. 5 is a cross-sectional view of the embodiment of an intravascular device delivery system of FIG. 3 in a left atrium.

FIG. 5 shows the embodiment of an elongated member 302 and rigid intravascular device 308 of FIG. 3 positioned in left atrium 310 of the heart 334. In some embodiments, the target location is the mitral annulus 306. The rigid intravascular device 308 may have a longitudinal length such that the rigid intravascular device 308 strikes the wall of the left atrium 310 opposite the intra-atrial septum 322 if the distal tip 304 of the elongated member 302 is positioned over the mitral annulus 306 before deflecting the elongated member 302.

In some embodiments, the elongated member 302 is advanced until the distal tip of the outer sleeve 324 is positioned just beyond the intra-atrial septum in the left atrium 310, such that the rigid intravascular device 308 is in the left atrium 310 and little to no longitudinal length of the outer sleeve 324 is in the left atrium 310. For example, less than 5 mm, less than 4 mm, less than 3 mm, less than 2 mm, or less than 1 mm of the outer sleeve 324 may be located in the left atrium 310.

Figures 1, 6:
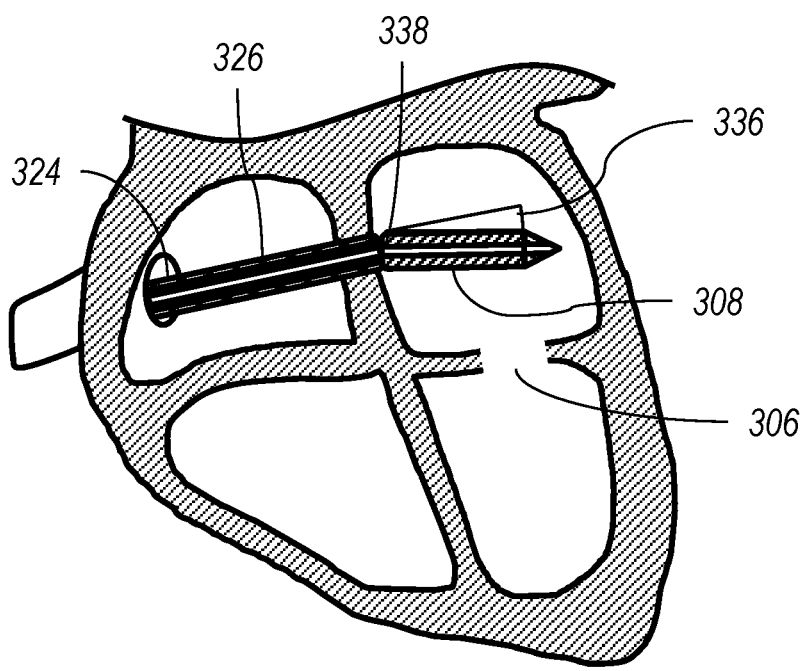
Figures 2, 6:
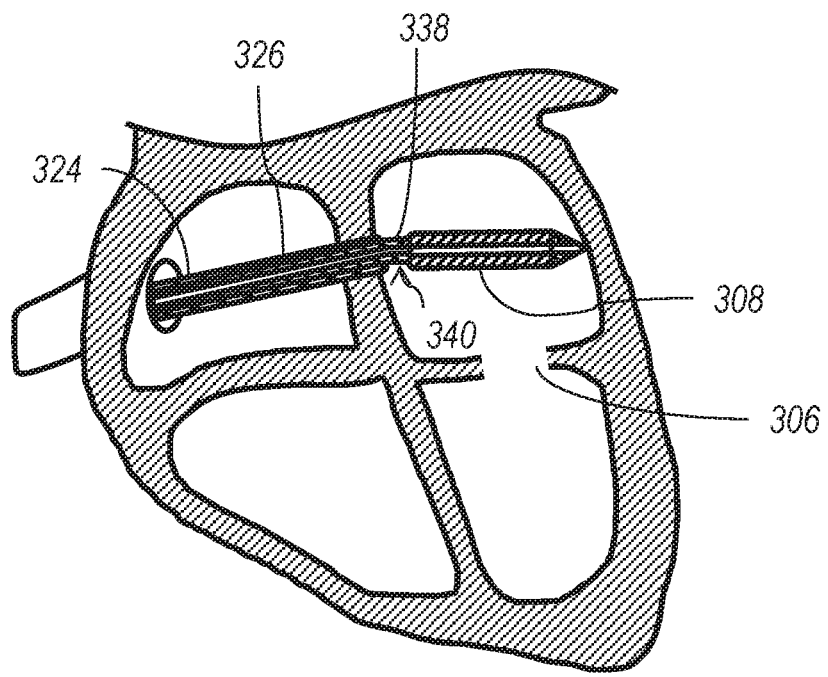

As shown in FIG. 6-1, the rigid intravascular device 308 may be deflected toward the target location (e.g., downward toward the mitral annulus 306). The rigid intravascular device 308 may be deflected by steering the inner steerable catheter 326 toward the target location, by steering the outer sleeve 324 toward the target location, or a combination thereof. The rigid intravascular device 308 may be deflected by a deflection angle 336 in a range having an upper value, a lower value, or an upper and lower value including any of 5°, 10°, 15°, 20°, 25°, 30°, 35°, 40°, 45°, 50°, 55°, 60°, 65°, 70°, 75°, 80°, 85°, 90°, 95°, 100°, or any values therebetween. For example, the deflection angle 336 may be greater than 5°. In other examples, the deflection angle 336 may be less than 100°. In yet other examples, the deflection angle 336 may be between 5° and 100°. In further examples, the deflection angle 336 may be between 10° and 90°.

FIG. 6-2 illustrates the rigid intravascular device 308 and inner steerable catheter 326 being advanced relative to the outer sleeve 324. The inner steerable catheter 326 is moved longitudinally through the outer sleeve 324 such that the rigid intravascular device 308 moves distally and away from the outer sleeve 324. A deflection portion 338 of the inner steerable catheter 326 is located at or near the distal tip of the inner steerable catheter 326 such that longitudinal movement of the inner steerable catheter 326 moves the deflection portion 338 relative to at least one of the outer sleeve 324, the intra-atrial septum, and the mitral annulus 306.

In some embodiments, the inner steerable catheter 326 is advanced relative to the outer sleeve 324 a longitudinal distance 340 in a range having an upper value, a lower value, or an upper and lower value including any of 0.5 mm, 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, or any values therebetween. For example, the inner steerable catheter 326 is advanced relative to the outer sleeve 324 a longitudinal distance 340 greater than 0.5 mm. In other examples, the inner steerable catheter 326 is advanced relative to the outer sleeve 324 a longitudinal distance 340 less than 10 mm. In yet other examples, the inner steerable catheter 326 is advanced relative to the outer sleeve 324 a longitudinal distance 340 in a range between 0.5 mm and 10 mm.

After advancing the inner steerable catheter 326 relative to the outer sleeve 324, the rigid intravascular device 308 may be deflected toward the target location (e.g., downward toward the mitral annulus 306) a second time, similar to as described in relation to FIG. 6-1. In some embodiments, the rigid intravascular device 308 is deflected a second deflection amount that is greater than the first deflection amount of the first time. In other embodiments, the rigid intravascular device 308 is deflected a second deflection amount that is less than the first deflection amount of the first time. In yet other embodiments, the rigid intravascular device 308 is deflected a second deflection amount that is equivalent to the first deflection amount of the first time.

In some embodiments, after the rigid intravascular device 308 is deflected a second time, the inner steerable catheter 326 is advanced relative to the outer sleeve 324 a second time, similar to as described in relation to FIG. 6-2. In some embodiments, the inner steerable catheter 326 is advanced relative to the outer sleeve 324 a second longitudinal distance that is greater than the first longitudinal distance of the first time. In other embodiments, the inner steerable catheter 326 is advanced relative to the outer sleeve 324 a second longitudinal distance that is less than the first longitudinal distance of the first time. In yet other embodiments, the inner steerable catheter 326 is advanced relative to the outer sleeve 324 a second longitudinal distance that is equivalent to the first longitudinal distance of the first time.

In at least one embodiment, deflecting the rigid intravascular device 308 and advancing the inner steerable catheter 326 relative to the outer sleeve 324 are at least partially simultaneous. For example, an operator may deflect the rigid intravascular device 308 while advancing the inner steerable catheter 326 relative to the outer sleeve 324.

Figure 7:
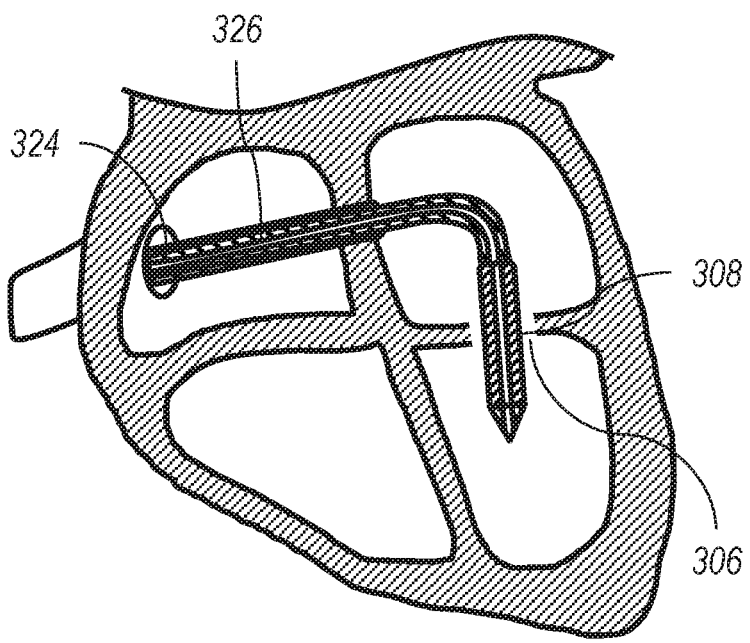
FIG. 7 is a cross-sectional view of the embodiment of an intravascular device delivery system of FIG. 3 with the intravascular device positioned at the mitral valve.

An operator may deflect the rigid intravascular device 308 and advance the inner steerable catheter 326 relative to the outer sleeve 324 until the rigid intravascular device 308 is positioned at the target location, as shown in FIG. 7. In at least one embodiment, the target location is the mitral annulus 306 of the heart. Once positioned at the target location, the rigid intravascular device 308 may be oriented substantially normal to the mitral annulus 306 by rotational deflection of the inner steerable catheter 326 relative to the outer sleeve 324.

In some embodiments, the rigid intravascular device 308 may be deployed at the target location and subsequently remain in the patient's body. In other embodiments, the rigid intravascular device 308 may be used to perform a therapeutic procedure at the target location and be subsequently removed from the patient's body.

The right atrium 332 of a human heart 334 provides limited space in which to bend or steer a catheter from the direction in which the inferior vena cava enters the heart to a direction in line with the intra-atrial septum separating the right atrium 332 from the left atrium 333. And, the longer an intravascular device 308 is, the more difficult it can be to make the necessary bend within the confines of the right atrium 332. For example, FIG. 8A graphically depicts a path generally taken by a conventional delivery catheter through the right atrium 332 and through the intra-atrial septum.

Figure 10:
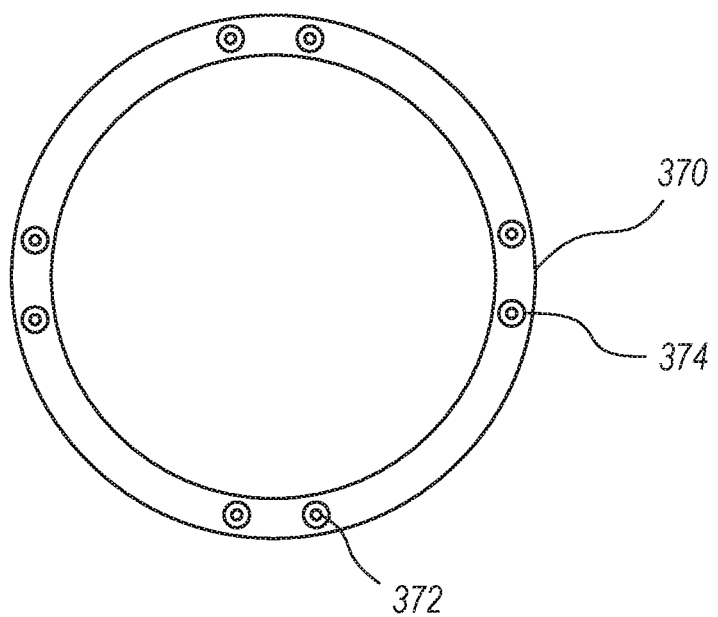
FIG. 10 is a cross-sectional view of an inner steering catheter.

To address that issue, the steerable outer sleeve 324 can produce a first bend at a first location 350 near a distal end of the steerable outer sleeve 324, while also producing a second bend at a second location 352 proximal the first location 350. This can provide an improved path for the delivery catheter, as graphically illustrated in FIG. 8B, that can provide additional space in which to allow the distal end portion of the catheter and intravascular device to make the turn within the right atrium. As mentioned above, the outer sleeve 324 can have various alternate configurations. In some embodiments, the outer sleeve 324 is a steerable catheter, such as a steerable guide catheter, that is steerable in at least one plane. For instance, in one configuration, the steerable outer sleeve 324 can bend or steer in two different directions within the same plane to aid positioning the elongated member 324 along the vena cava, as illustrated in FIGS. 8-10, to position the distal tip within the right atrium of the heart in preparation for advancement of the rigid intravascular device 308 through the intra-atrial septum and steering towards a deployment location in the left atrium of the heart. The second bend at the second location 352 can be in a direction opposite to that of the first bend at the first location 350. By so doing, the second bend pushes or "kicks" the steerable outer sleeve 324, and more generally the catheter, in the opposite direction from the movement of the distal tip near the first location 350. This movement urges the catheter near the first bend location 350 to move toward the wall of the right atrium 332 of the heart 334 and creates more space for the distal tip of the catheter (i.e., a distal portion of elongated member 302 and the rigid intravascular device 308) to bend and penetrate the intra-atrial septum.

The steerable outer sleeve 324 can be a hypotube, either based on stainless steel or Nitinol. Different sections of the hypotube can be cut in a way that causes that section to bend only in one, desired plane. As illustrated in FIG. 9, various cutting patterns can be used can be used in different sections or regions of the steerable outer sleeve 324 to produce the desired bends and locations 350 and 352. Each section can include cut patterns that can include one or more slits 356 and/or one or more island cuts 358. The slits 356 may transmit longitudinal force along the steerable outer sleeve 324 and allow expansion of the flexible steerable outer sleeve 324 when the flexible steerable outer sleeve 324 is deflected in a direction opposite the slit 356. The island cuts 358 may allow compression of the flexible steerable outer sleeve 324 when the flexible steerable outer sleeve 324 is deflected in a direction of the island cuts 358. For example, slits 356 and island cuts 358, when located on opposite sides from one another on a flexible steerable outer sleeve 324 may direct preferential bending of the steerable outer sleeve 324 along a center line of the island cuts 358.

In one embodiment, illustrated in FIG. 9, the cutting pattern formed in steerable outer sleeve 324 can include five sections or regions 360, 362, 364, 366 and 368, with different cut patterns in each section. For example, in the embodiment illustrated in FIG. 9: first section 360 can be approximately 2.5 mm in length and can consist of a plurality of holes radially spaced about the periphery of the steerable outer sleeve 324; second section 362 can be approximately 25 mm in length and can consist of approximately 43 slits and island cuts; third section 364 can be approximately 8 mm in length and can consist of approximately 14 slits and island cuts; fourth section 366 can be approximately 30.5 mm in length and can consist of an uncut distal portion that can be approximately 7 mm in length, a cut portion that can be approximately 35 mm in length and can include approximately 21 slits and island cuts and an uncut proximal portion that can be approximately 2.5 mm in length; and fifth section 368 can be approximately 570 mm in length and can consist of approximately 228 slits. While the island cuts 358 are depicted in FIG. 9 as diamond-shaped, the island cuts 358 may have one or more other shapes, such as square, rhombohedral, triangular, rectangular, circular, oblong, other elliptical, other polygonal, irregular, or combinations thereof.

To force the steerable outer sleeve 324 to bend, tension cables 372 can extend to rings 370 placed at different locations of the steerable outer sleeve 324. For instance, the tension cables 372 can be placed on an outside of the steerable outer sleeve 324 and extend through holes 374 in one or more rings 370, as shown in FIG. 10, before terminating in attachment to the steerable outer sleeve 324 directly or to one of the rings 370 placed to anchor the tension cables 372. Including a number of the rings 370 along the length of the steerable outer sleeve 324 and passing the tension cables 372 avoids weakening the strength of the tension cable 372. The rings 370 can be laser welded to the steerable outer sleeve 324.

It will be understood that the tension cables 372 can be routed through lumens in the wall of the steerable outer sleeve 324, through an inner lumen of the outer sleeve 324, along grooves formed on an interior or exterior surface of the steerable outer sleeve 324, or by some other structure or manner to route the tension cables.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A method of positioning an intravascular device delivery system at a target location, the method comprising:
   positioning a portion of an elongated member within a vena cava, a first bend portion of the elongated member being near a distal tip of the elongated member and a second bend portion of the elongated member being proximal the first bend portion, the second bend portion being disposed within the vena cava and bending in a direction opposite to the first bend portion;
   positioning a distal tip of the elongated member of the intravascular device delivery system in a right atrium of a heart, the distal tip being urged toward a wall of the right atrium of the heart by the combination of the first bend portion and the second bend portion;
   moving the distal tip of the elongated member into a left atrium of the heart while the second bend portion is within the vena cava and the first bend portion is within the right atrium;
   moving an inner steerable catheter of the elongated member relative to an outer sleeve of the elongated member, the inner steerable catheter steering the outer sleeve of the elongated member;
   deflecting at least a portion of the inner steerable catheter a first deflection amount within the left atrium towards a mitral annulus; and
   deflecting at least a portion of the inner steerable catheter a second deflection amount within the left atrium towards the mitral annulus.

2. The method of claim 1, further comprising advancing the inner steerable catheter of the elongated member longitudinally distally relative to the outer sleeve of the elongated member a first longitudinal distance and deflecting at least the portion of the inner steerable catheter the first deflection amount at least partially simultaneously.

3. The method of claim 2, further comprising advancing the inner steerable catheter of the elongated member longitudinally distally relative to the outer sleeve of the elongated member a second longitudinal distance and deflecting at least the portion of the inner steerable catheter the second deflection amount at least partially simultaneously.

4. The method of claim 3, wherein the second longitudinal distance is less than 10 millimeters.

5. The method of claim 2, wherein the first longitudinal distance is less than 10 millimeters.

6. The method of claim 1, wherein the first deflection amount is less than 90°.

7. The method of claim 1, wherein the second deflection amount is less than 90°.

8. The method of claim 1, wherein moving the distal tip of the elongated member in the left atrium of the heart further comprises positioning a distal tip of the outer sleeve of the elongated member in the left atrium within 10 mm of an intra-atrial septum.

9. The method of claim 1, further comprising deflecting the outer sleeve in a direction opposite to a direction of the distal tip of the elongated member of the intravascular device delivery system in the right atrium of the heart.

10. The method of claim 1, further comprising deflecting the outer sleeve at a location proximal a distal location about which the distal tip of the elongated member of the intravascular device delivery system deflects to position the distal tip in the right atrium of the heart.

11. A method of positioning an intravascular device delivery system at a target location, the method comprising:
    positioning a replacement valve in a right atrium of a heart, the replacement valve located at a distal end of an elongated member of the intravascular device delivery system and distal a distal end of an inner steerable catheter disposed within an outer sleeve of the elongated member, wherein positioning the replacement valve comprises positioning a portion of the elongated member within a vena cava, a first bend portion of the elongated member being near the distal end of the elongated member and a second bend portion of the elongated member being proximal the first bend portion, the second bend portion being disposed within the vena cava and bending in a direction opposite to the first bend portion to urge a portion of the first bend portion toward a wall of the right atrium of the heart at a junction of the vena cava and the right atrium;
    moving a distal tip of the elongated member into a left atrium of the heart while the second bend portion is within the vena cava and the first bend portion is within the right atrium;
    moving the replacement valve into the left atrium of the heart;
    deflecting at least a portion of the inner steerable catheter a first deflection amount within the left atrium towards a mitral annulus;
    deflecting at least a portion of the inner steerable catheter a second deflection amount within the left atrium towards the mitral annulus; and
    deploying the replacement valve at the target location.

12. The method of claim 11, further comprising advancing the inner steerable catheter of the elongated member longitudinally distally relative to the outer sleeve of the elongated member a first longitudinal distance and deflecting at least the portion of the inner steerable catheter the first deflection amount at least partially simultaneously.

13. The method of claim 12, further comprising advancing the inner steerable catheter of the elongated member longitudinally distally relative to the outer sleeve of the elongated member a second longitudinal distance and deflecting at least the portion of the inner steerable catheter the second deflection amount at least partially simultaneously.

14. The method of claim 13, wherein the second longitudinal distance is less than 6 millimeters.

15. The method of claim 12, wherein the first longitudinal distance is less than 6 millimeters.

16. The method of claim 11, wherein a longitudinal length of the replacement valve is greater than 10 millimeters.

17. The method of claim 11, wherein the first deflection amount is less than 45°.

18. The method of claim 11, wherein the second deflection amount is less than 45°.

19. The method of claim 11, wherein moving the distal tip of the elongated member in the left atrium of the heart further comprises positioning a distal tip of the outer sleeve of the elongated member in the left atrium within 10 mm of an intra-atrial septum.

20. The method of claim 11, further comprising deflecting the outer sleeve in a direction opposite to a direction of movement of the distal tip of the elongated member of the intravascular device delivery system in the right atrium of the heart.

21. The method of claim 11, further comprising deflecting the outer sleeve at a location proximal a distal location about which the distal tip of the elongated member of the intravascular device delivery system deflects to position the distal tip in the right atrium of the heart.

22. A method of positioning an intravascular device delivery system at a target location, the method comprising:

positioning a replacement valve in a right atrium of a heart, the replacement valve located at a distal end of an elongated member of the intravascular device delivery system and the replacement valve having a longitudinal length at least 10 millimeters, wherein positioning the replacement valve comprises positioning a portion of the elongated member within a vena cava, a first bend portion of the elongated member being near the distal end and a second bend portion of the elongated member being proximal the first bend portion, the second bend portion bending in a direction opposite to the first bend portion to urge the elongate body near the first bend portion toward a wall of the right atrium of the heart;

moving the rigid intravascular device into a left atrium of the heart through an intra-atrial septum while the second bend portion is within the vena cava and the first bend portion is within the right atrium;

moving an inner steerable catheter of the elongated member relative to an outer sleeve of the elongated member with the replacement valve disposed distal a distal end of the inner steerable catheter;

deflecting at least a portion of the inner steerable catheter a first deflection amount within the left atrium towards a mitral annulus;

deflecting at least the portion of the inner steerable catheter a second deflection amount within the left atrium towards the mitral annulus;

longitudinally positioning the inner steerable catheter of the elongated member relative to the outer sleeve of the elongated member a first longitudinal distance within the left atrium; and deploying the replacement valve at the target location.

* * * * *